US007989194B2

(12) United States Patent
Seeger Pfeiffer et al.

(10) Patent No.: US 7,989,194 B2
(45) Date of Patent: Aug. 2, 2011

(54) PCB-DEGRADING RECOMBINANT BACTERIUM, PRODUCT FOR THE BIOREMEDIATION AND METHOD OF BIOREMEDIATION

(75) Inventors: Michael Seeger Pfeiffer, V Region (CL); Juan Matías Saavedra Salinas, V Region (CL); Francisca Acevedo Canala-Echevarria, V Region (CL)

(73) Assignee: Universidad Tecnica Federico Santa Maria, Valparaiso, V Region (CL)

( * ) Notice: Subject to any disclaimer, the term of this patent is extended or adjusted under 35 U.S.C. 154(b) by 826 days.

(21) Appl. No.: 11/767,221

(22) Filed: Jun. 22, 2007

(65) Prior Publication Data

US 2008/0318302 A1 Dec. 25, 2008

(51) Int. Cl.
*C12N 1/20* (2006.01)
*A62D 3/00* (2007.01)
(52) U.S. Cl. .................. 435/252.3; 435/262.5; 424/93.2
(58) Field of Classification Search .......................... None
See application file for complete search history.

(56) References Cited

U.S. PATENT DOCUMENTS

| | | | |
|---|---|---|---|
| 4,843,007 A | 6/1989 | Bedard et al. |
| 4,843,009 A | 6/1989 | Bopp |
| 5,009,999 A | 4/1991 | Bopp |
| 5,897,996 A | 4/1999 | Kimbara et al. |
| 5,968,360 A | 10/1999 | Crowley et al. |
| 6,083,738 A | 7/2000 | Moser et al. |
| 6,287,842 B1 | 9/2001 | Dyadischev |
| 6,537,797 B1 | 3/2003 | Picardal et al. |
| 2003/0148501 A1 | 8/2003 | Picardal et al. |

FOREIGN PATENT DOCUMENTS

| | | |
|---|---|---|
| CL | 2816-2004 | 10/2004 |
| JP | 2000069967 | 3/2000 |
| JP | 2004298058 | 10/2004 |
| WO | WO 03065011 | 8/2003 |

OTHER PUBLICATIONS

Valenzuela et al., Applied and Environmental Microbiology, vol. 63, No. 1, Jan. 1997, p. 227-232.*
Saavedra et al., Appl Microbiol Biotechnol (2010) 87:1543-1554.*
Kalmaz et al., Transport, Distribution and Toxic Effects of Polychlorinated Biphenyls in Ecosystems: Review, Ecol. Model 6:223-251; 1979.
Mokross et al., Degradation of 3-chlorobiphenyl by in vivo constructed hybrid pseudomonads, FEMS Microbiol. Lett. 71:179-186; 1990.
Havel et at., Total degradation of various chlorobiphenyls by cocultures and in vivo constructed hybrid pseudomonads, FEMS Microbiol. Lett. 78:163-170; 1991.
Adams et al., Construction of a 3-Chlorobiphenyl-Utilizing Recombinant from an Intergeneric Mating, Appl. Environ Microbial., 58:647-654; Feb. 1992.
Hofer et al., Pseudomonads Designed for Bioremediation and Circumvention of Undesirable Routes, Molecular Biology of Pseudomonads, Chapter 10, pp. 121-129, 1996.
Potrawfke et al., Mineralization of low-chlorinated biphenyls by Burkholderia sp. strain LB400 and by a two-membered consortium upon directed interspecies transfer of chlorocatechol pathway genes, Appl Microbiol. Biotechnol., 50:440-446; 1998.
Hrywna et al., Construction and Characterization of Two Recombinant Bacteria That Grow on ortho- and para-Substituted Chlorobiphenyls, Appl. Environ. Microbiol, 65:2163-2169; May 1999.
Klemba et al., Chromosomal Integration of tcb Chlorocatechol Degradation Pathway Genes as a Means of Expanding the Growth Substrate Range of Bacteria to Include Haloaromatics, Appl. Environ. Microbiol., 66:3255-3261; Aug. 2000.
Rodrigues et al., Development of Rhodococcus Recombinant Strain for Degradatio of Products from Anaerobic Dechlorination of PCBs, Environ. Scien. Technol., 35:663-668; 2001 (Publ. On Web Dec. 28, 2000).
Sanggoo et al., Microbial Growth on Dichlorobiphenyls Chlorinated on Both Rings as a Sole Carbon and Energy Source, Appl. Environ. Microbial., 67:1953-1955; Apr. 2001.
Beltrametti et al., Analysis of transcription of the *bph* locus of Burkholderia sp. strain LB400 and evidence that the ORF0 gene product acts as a regulator of the *bphA1* promoter, Microbiology, 2001, vol. 147, pp. 2169-2182.
Clement et al., Molecular characterization of a deletion/duplication rearrangement in tfd genes from *Ralstonia eutropha* JMP134(pJP4) that improves growth on 3-chlorobenzoic acid but abolishes growth on 2,4-dichlorophenoxyacetic acid, Microbiolgy, 2001, vol. 147, pp. 2141-2148.
Dowling et al., A DNA module encoding bph genes for the degradation of polychlorinated byphenyls (PCBs), FEMS Microbiology Letters 113, 1993, pp. 149-154.
Ledger et al., Novel insights into the interplay between peripheral reactions encoded by xyl genes and the chlorocatechol pathway encoded by tfd genes for the degradation of chlorobenzoates by *Ralstonia eutropha* JMP134, Microbiology, Nov. 2002, vol. 148, pp. 3431-3440.
Ohtsubo et al., Novel Approach to the Improvement of Biphenyl and Polychlorinated Biphenyl Degradation Activity: Promoter Implantation by Homologous Recombination, Applied and Environmental Microbiology, Jan. 2003, vol. 69, No. 1, pp. 146-153.
Perez-Pantoja et al., Efficient Turnover of Chlorocatechols Is Essential for Growth of *Ralstonia eutropha* JMP134(pJP4) in 3-Chlorobenzoic Acid, Journal of Bacteriology, Mar. 2003, vol. 185, No. 5, pp. 1534-1542.
Singer et al., Bioremediation of polychlorinated biphenyl-contaminated soil using carvone and surfactant-grown bacteria, Appl Mircobiol Biotechnol, 2000, vol. 54, pp. 838-843.

* cited by examiner

*Primary Examiner* — Irene Marx
(74) *Attorney, Agent, or Firm* — Hasse & Nesbitt LLC; Daniel F. Nesbitt

(57) ABSTRACT

A recombinant bacterium capable to completely degrade or mineralize pollutants such as polychlorobiphenyls (PCBs), which corresponds to *Cupriavidus necator* strain JMS34, deposited under the access number NRRL B-30817 a product for the bioremediation of environments contaminated with PCBs, where the product includes a bacterial inoculum of this recombinant strain and a method for the bioremediation of environments contaminated with PCBs, which uses this product for the bioremediation.

19 Claims, 3 Drawing Sheets

PCB-DEGRADING RECOMBINANT BACTERIUM, PRODUCT FOR THE BIOREMEDIATION AND METHOD OF BIOREMEDIATION

The present invention relates to the recombinant bacterium *Cupriavidus necator* JMS34, which degrades polychlorobiphenyls, the preparation process thereof, a product for the bioremediation which contains this bacterium and a bioremediation method for environments contaminated with polychlorobiphenyls.

BACKGROUND OF THE INVENTION

Polychlorobiphenyls (PCB) are synthetic chlorinated organic compounds derived from biphenyl. They are 209 congeners of PCBs, which differ in the number and position of chlorine atoms on the biphenyl backbone.

Polychlorobiphenyls (PCB) are environmental pollutants which causes great problems. PCBs are globally distributed compounds, characterized by their non reactive chemical structure and low water solubility. In general these compounds are considered non degradable (Kalmaz et al., 1979, Review. Ecol. Model 6:223-251). PCB-contaminated waste is a major component of many polluted environmentally hazardous sites, which require treatment or remediation.

PCBs were mainly produced and commercialized in North America, Europe and Japan during 60 years, from the beginning of the 1930s. The commercial mixtures of the PCBs such as Aroclor (Monsanto, United States), Phenoclor and Pyralene (Prodelec S.A., France), Clophen (Bayer AG, Germany) and Kanechlor (Kanegafuchi Chemical Industrial Co. Ltd., Japan) contain between about 60 and 80 different congeners. PCBs have been used in the industry as dielectrics fluids in transformers and capacitors, hydraulic and heat transfer fluids and fire retardants, among other applications. In addition, they could be in lubricants, paints, plastics and adhesives. The enormous industrial application of these compounds is due to their extraordinary physical and chemical properties, i.e., oily consistency, great stability, chemical inertia, heat resistance and high dielectric constant. Nevertheless, the chemical stability of PCBs also prevents its degradation in the environment. On the other hand, the high hydrofobicity of these compounds allows their solubility in organic solvents, oils and fats, which promotes their accumulation through the trophic chains. This phenomenon is known as biomagnification. PCBs have been detected worldwide, including non-industrialized zones located away from their industrial sources such as the poles. PCBs cause world-wide concern after the accidental contamination of rice oil in Japan and Taiwan by the end of 1968 and 1979, respectively. These events related PCBs to serious effects on human and animal health (Yao et al., 2002; Chen et al., 1992). Due to these events the international community becames aware of the necessity to regulate the production, use and elimination of the PCBs. Different types of cancer have been related to these compounds, especially liver and digestive system cancers. PCBs has been related also with reproductive disorders, development deficiencies, anomalies in the immunological system, endocrine system disorders, neurological damages and cutaneous injuries. In May, 2001 during the Convention of Stockholm, the problem of the persistent organic pollutants (POPs) was discussed. As a result a list of 12 POPs including the PCBs were classified as POPs for priority action. In 1976, in the United States as well as in Europe the first legal figures were established to limit and to eventually erradicate the commercialization and manipulation of PCBs. In Chile the use of PCBs in new electrical equipments such as transformers and converters is actually forbidden. Nevertheless, electrical equipment containing PCBs, which were produced before the date of prohibition, are still used. According to the project entitled "National Diagnosis of Persistent Organic Pollutants" promoted by the CONAMA (Spanish acronym of Environmental National Commission), there are huge amounts of PCBs stored and in use in Chile (at least 396,705 liters). The II and III regions have the main amounts of PCBs followed by the VIII and Metropolitan regions (Eula-Chile Center, 2001). Different PCB congeners have been detected in bivalves, fish muscle, bird eggs and muscle and sediments in different regions of the country (Focardi et al., 1996; Fuentealba, 1997; Muñoz and Becker, 1999; Barra et al., 2004). Different methods are currently known to destroy PCBs. These methods are based on physical, chemical or physicochemicals processes such as incineration, thermal desortion, chemical dechlorination, solvent extraction, ground washing and immobilization. Nevertheless, all these techniques involve expensive operation costs and most of them cannot be applied to contamination sites of wide water or soil extensions. The biological degradation by microorganisms represents an attractive alternative for the implementation of bioprocesses for the elimination of PCBs and the remediation of soil contaminated with these compounds.

Diverse microorganisms capable of degrading biphenyls and their chlorinated derivatives, both in aerobic and anaerobic conditions have been described. The aerobic bacterial degradation have been widely studied, which allowed the characterization of a complete catabolic route. Diagram 1 represents the aerobic process of biodegradation of PCBs.

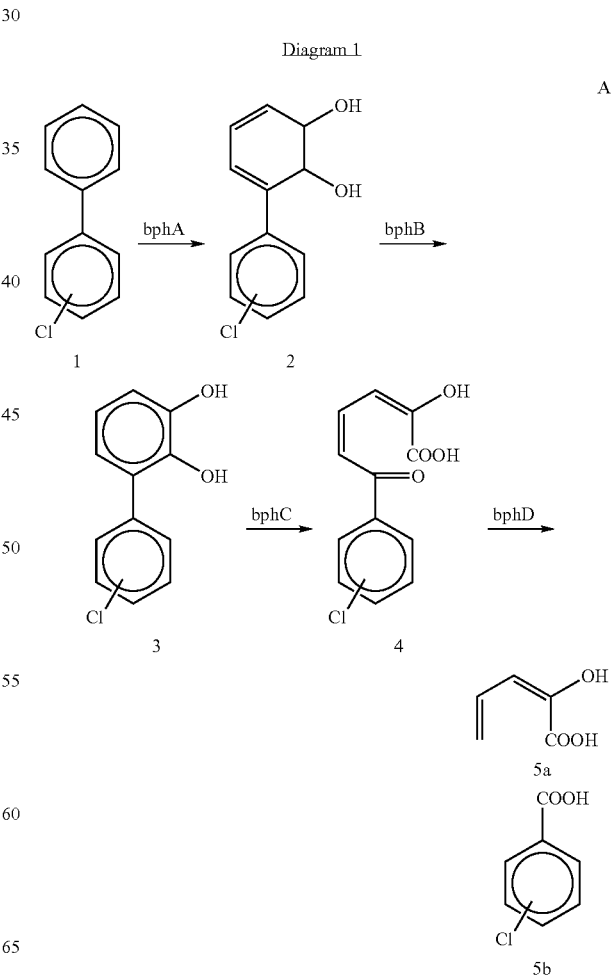

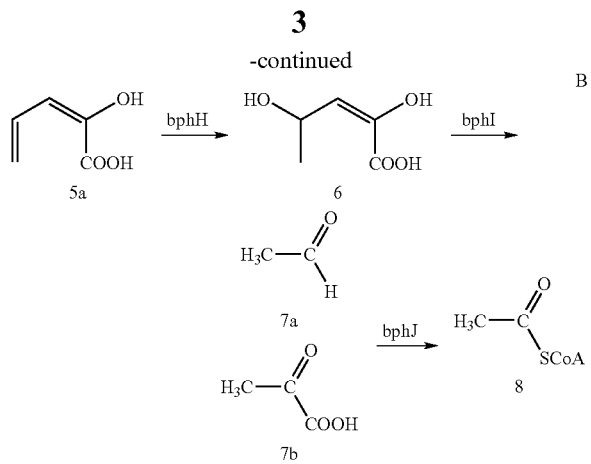

The compound (chloro)biphenyl (1) is dioxygenated by a biphenyl-2,3-dioxygenase to form the product biphenyl-dihydrodiol (2). This compound is then dehydrogenated by a biphenyl-dihydrodiol dehydrogenase to form 2,3-dihydroxybiphenyl (3). Subsequently, a new dioxygenation carried out by a 2,3-dihydroxybiphenyl-1,2-dioxygenase generate the compound 2-hydroxy-6-oxo-6-phenyl-hexa-2,4-dienoate (4). This compound is finally transformed by an hydrolase into 2-hydroxypenta-2,4-dienoate (5a) and (chloro)benzoate (5b). This step is the last reaction of the upper biphenyl degradation pathway. The lower catabolic pathway catalyzes the oxidation of 2-hydroxypenta-2,4-dienoate (5a) into intermediates of the metabolism to yield energy. As a first stage of the lower pathway, a hydratase produces the compound 4-hydroxy-2-oxovalerate (6). Then an aldolase produces the compounds acetaldehyde (7a) and piruvate (7b). The last step of the lower biphenyl pathway is the acetaldehyde CoA generation by an acetaldehyde dehydrogenase.

The bacterium *Burkholderia xenovorans* LB400, which was isolated about the middle of the 1980s by a team of the General Electric company from a garbage dump contaminated with chloroaromatics in the state of New York, U.S.A., is one of the most potent PCB-degrading microorganism. This bacterium is capable to attack a wide range of highly-chlorinated congeners including hexachlorinates ones due to the relaxed specificity of its catabolic enzymes. Nevertheless, like most of the PCB-degrading strains, which have been characterized until now, it is not capable to degrade chlorobenzoates (CBA). This leads to the accumulation of CBAs during the bacterial degradation of PCBs. This can lead to the potential generation of highly toxic compounds by the environmental microflora such as the protoanemonin antibiotic. This phenomenon considerably decreases the degradative process and constitutes a significant problem for designing bioremediation strategies for PCBs. In order to avoid this problem and to improve the PCB bioremediation, several studies have been carried out to obtain microorganisms and microbial consortia that are capable to degrade a wide range of PCBs as well as CBAs. Some of these efforts to obtain an optimal biological system for PCB-remediation are: U.S. Pat. No. 4,843,007, Bedard et al., Jun. 27, 1989; U.S. Pat. No. 4,843,009, Bopp, Jun. 27, 1989; U.S. Pat. No. 5,009,999, Bopp, Apr. 23, 1991; U.S. Pat. No. 5,968,360, Crowley et al., Oct. 19, 1999; U.S. Pat. No. 6,287,842, Dyadischev et al., Sep. 11, 2001; U.S. Pat. No. 3,148,501, Sanggoo and Flynn, Aug. 7, 2003. The following publications are also included: Mokross et al., 1990, FEMS Microbiol. Lett. 59:179-185; Havel and Reineke, 1991, FEMS Microbiol. Lett. 62:163-169; Adams et al., 1992, Appl. Environ. Microbiol., 58:647-654; Hofer et al., 1996, Molecular Biology of Pseudomonads; Potrawfke et al., 1998, Appl. Microbiol. Biotechnol. 50:440-446; Hrywna et al., 1999. Appl. Environ. Microbiol, 65:2163-2169; Klemba et al., 2000, Appl. Environ. Microbiol. 66:3255-3261; Rodrigues et al., 2001, Environ. Scien. Technol. 35:663-668; Sanggoo et al., 2001, Appl. Environ. Microbiol. 67:1953-1955.

The construction of recombinant bacteria with improved PCB-degrading capacities have been not very successful. This could be explained by the limited substrate range of the bacteria, and the poorly known genetic systems. A way to overcome these limitations is to use well-characterized systems with known catabolic capabilities.

SUMMARY OF THE INVENTION

The present invention relates to a recombinant bacterium, which is capable to completely degrade or mineralize diverse polychlorobiphenyls (PCBs).

In one aspect of the present invention these compounds are selected from monochlorinated- and dichlorinated biphenyls.

In a second embodiment of the present invention the monochlorinated biphenyls are selected from 3-chlorobiphenyl (3-CB) and 4-chlorobiphenyl (4-CB); and the dichlorinated biphenyls are selected from 3,5-dichlorobiphenyl (3,5-dCB) and 2,4'-dichlorobiphenyl (2,4'-dCB).

In an additional embodiment of the present invention this recombinant bacterium is capable to completely degrade or mineralize the compounds 3-chlorobenzoate (3-CBA), 4-chlorobenzoate (4-CBA) and 3,5-dichlorobenzoate (3,5-dCBA), which are metabolic intermediates of the degradation of 3-CB, 4-CB, 3,5-dCB and 2,4'-dCB.

In a preferred embodiment of the invention this recombinant bacterium is the strain *Cupriavidus necator* JMS34 deposited under the access number NRRL B-30817 at Jan. 31, 2005, which is capable to completely degrade or mineralize PCB congeners.

In an additional embodiment of the invention this strain *Cupriavidus necator* JMS34 is capable to completely degrade or mineralize PCB congeners in the presence of m-toluate (3-methylbenzoate).

The present invention also includes a method for the treatment or bioremediation of an environment contaminated with PCBs, wherein this method comprises the stages of i) adding a recombinant bacterium to this environment contaminated with PCBs, where this bacterium is capable to completely degrade or mineralize a PCBs, and where the PCBs contain from one to three chlorine atoms bound to the biphenyl backbone, and ii) incubating this bacterium in the contaminated environment during a period of time sufficient to permit the complete degradation of the PCBs in the environment, and the bioremediation thereof. In addition, the present invention includes a method to improve the bioremediation of the contaminated environment with PCBs, where this method comprises the stages of i) adding a recombinant bacterium, which was previously cultivated in the presence of an compound that induces the xylXYZL genes, to this environment contaminated with PCBs, where this bacterium is capable to completely degrade or mineralize PCBs, and where these PCBs contain from one to three chlorine atoms bound to the biphenyl backbone and ii) incubating this bacterium in the contaminated environment during a period of time sufficient to permit the complete degradation of these PCBs in the environment, and the bioremediation thereof.

DETAILED DESCRIPTION OF THE INVENTION

Figure 1:
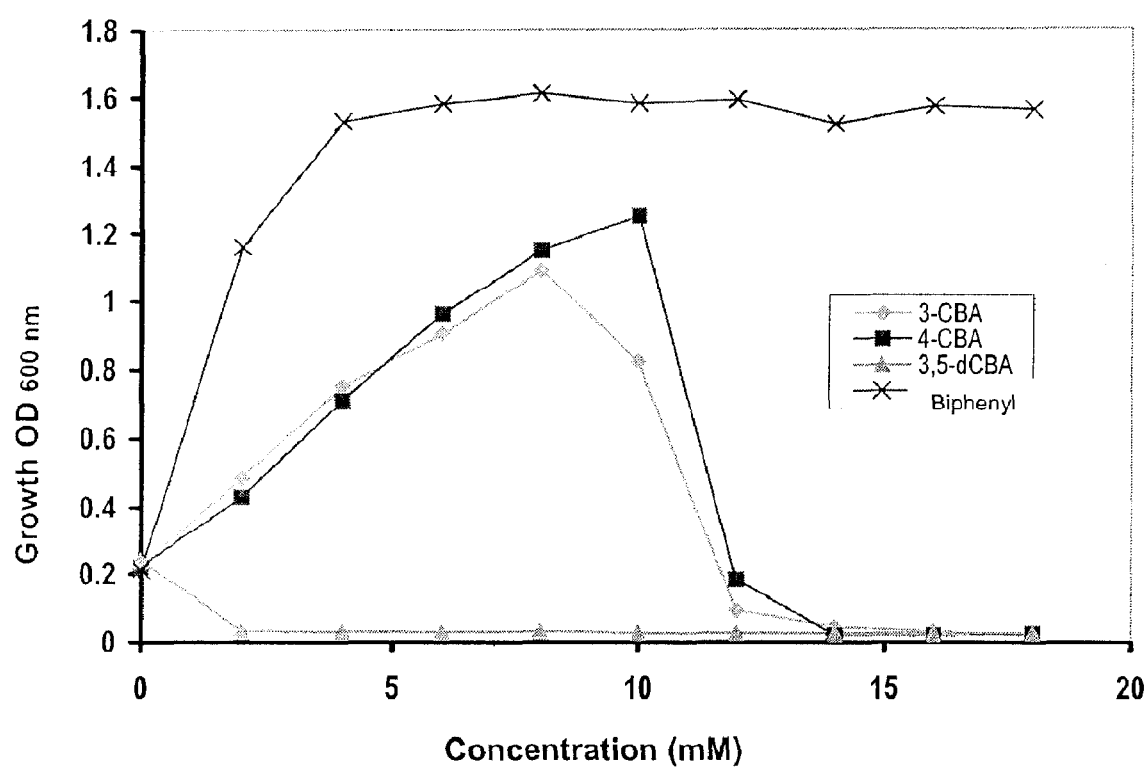
FIG. 1 shows the final growth (optical density) reached by cultures of *Cupriavidus necator* JMS34 using different concentrations of biphenyl, 3-CBA, 4-CBA and 3,5-dCBA as single carbon and energy source.

The present invention is related to a recombinant bacterium which is capable to completely degrade or mineralize polychlorobiphenyls (PCBs), and to a method of bioremediation of environment contaminated with PCBs, where this bacterium is constructed based on a strain that is capable to degrade CBAs known as *Cupriavidus necator* JMP134::X(pJP4-F3) (Ledger et al., 2002; Perez-Pantoja et al., 2003), to which the genetic bph locus of the strain *Burkholderia xenovorans* LB400 encoding the complete chlorobiphenyl catabolic pathways has been incorporated.

*Cupriavidus necator* has also been known as *Wautersia eutropha*. Strains classified as *Cupriavidus necator* and *Wausteria eutropia* are the same species, and in fact strains classified as *Cupriavidus necator*, *Wausteria eutropia*, *Ralstonia eutropha* and *Alcaligenes eutropha* are all the same species, each having been identified and named independently at different times. As the name *Cupriavidus necator* has taxonomic priority over the names *Wausteria eutropia*, *Ralstonia eutropha* and *Alcaligenes eutropha*, the strain is identified as *Cupriavidus necator*.

DEFINITIONS

As used in the present invention "polychlorobiphenyl" (PCB) refers to a molecule of biphenyl which binds at least one chlorine atom in its carboned backbone.

As used in the present invention the term "dichlorinated biphenyl" refers to a molecule of biphenyl that binds two chlorine atoms in its carboned backbone, where both chlorine atoms can be bound to the same aromatic ring or to both aromatic rings.

As used in the present invention the term "monochlorinated biphenyl" refers to a biphenyl which binds a single chlorine atom in its carboned backbone.

As used in the present invention the term "PCB congeners" means two or more isomers of a PCB compound.

As used in the present invention the term "degradation" refers to the decomposition of a chemical compound such as a PCB by a metabolic pathway to obtain a molecule of lower complexity. This chemical compound can be used or not as a carbon source in the metabolism of the microorganism, or can be used or not as the only carbon source for the microbial growth. For example, a PCB compound can be finally degraded to a chlorobenzoate molecule, which can be further used as carbon source for the growth of this microorganism.

As used in the present invention the term "mineralize" means the biological decomposition of an organic compound such as a PCB compound, into molecules of minimal complexity such as, e.g., the decomposition of a PCB compound into $H_2O$, $CO_2$ and HCl.

As is used in the present invention the term "bioremediation" means a treatment method to treat an environment or material considered as contaminated waste material located in a defined environment, where said treatment allows transforming this waste material into a material less toxic for the surrounding environment, or transforming this waste material into a material which can be metabolized by a microorganism or group of microorganisms, where this treatment method comprises the application of a living organism as a component of the treatment method.

As is used in the present invention the term "recombinant bacterium" means a bacterium containing a exogenous recombinant deoxyribonucleic acid that were not in this bacterium before the recombination. An amplified or assembled recombinant deoxyribonucleic acid can be included in a vector, and this vector can be used to transform a host cell.

The bacterium *Cupriavidus necator* JMP134::X (pJP4-F3) is a recombinant strain, which derives from *Cupriavidus necator* JMP134, but with improved properties for the degradation of CBAs. The strain *Cupriavidus necator* JMP134 is a Gram-negative bacterium isolated in Australia at the beginning of 1980s, characterized by its capability to grow using as carbon source the herbicide 2,4-dichlorophenoxyacetic acid (2,4-D). This strain is one of the known microorganisms more versatile for the mineralization of chloroaromatic compounds of one ring. The catabolic pathways and their genes of this strain have been extensively studied, and the genome of this bacterium has been recently sequenced. Strain JMP134 is capable to mineralize 3-chlorobenzoate due to well characterized genes that are located in the chromosome as well as in the conjugative plasmid pJP4 of 88 kb. The strain JMP134::X(pJP4-F3) was obtained by incorporating the xylXYZL genes and the xylS regulator gene from the catabolic plasmid pWWO of *Pseudomonas putida* mt-2, which codify the enzymes of the meta degradation pathway of xylene and toluene derivatives (also known as meta oxidation pathway), into the genome of a derivative strain of JMP134. This strain has a genetic rearrangement in plasmid pJP4, which produce the duplication of the catabolic genes related to the degradation of chloroaromatic compounds (Ledger et al., 2002; Perez-Pantoja et al., 2003). The enzyme codified by the xylXYZ genes is a toluate-dioxygenase of relaxed specificity, which provides the strain JMP134::X(pJP4-F3) with the capability to degrade 3-CBA, 4-CBA and 3,5-dCBA.

In a preferred embodiment of the present invention the bph genes were transferred into the genome of the strain JMP134::X(pJP4-F3) by a biparental conjugation with the suicidal vector pT5K012. This vector is derived from pUT-kan and contains the complete bph locus and a kanamycin resistance gene between the mini-Tn5 transposon ends. As the vector pT5K012 cannot replicate in the strain JMP134::X(pJP4-F3), clones in that the bph locus has been incorporated into the genome, can be isolated under selective conditions.

Construction of the *Cupriavidus necator* JMS34 Strain

The plasmid pT5K012 was transferred to *Cupriavidus necator* JMP134::X(pJP4-F3) through biparental mating, which is a known technique in the state of the art. The doner cells *Escherichia coli* SM10 (λpir), which contain plasmid pT5K012, and the recipient cells *Cupriavidus necator* JMP134::X(pJP4-F3), were cultivated in LB medium at 30° C. with rotatory agitation until exponential growth phase (O.D. from 0.5 to 0.8). Equal proportions of recipient and doner cells were used. Transconjugants were selected in LB agar plates containing merbromin (0.5 mM) and kanamycin (75 μg/ml).

The recombinant strain of the present invention was obtained, i.e., *Cupriavidus necator* JMS34, which showed interesting catabolic properties due to its capability to grow using biphenyl, 3-CBA and 4-CBA as the single carbon source.

Description of the Bacterial Strain *Cupriavidus necator* JMS34

The new strain *Cupriavidus necator* JMS34 has the bph locus in its genome, as a product of a single integration event. This was demonstrated by Southern blot using standard protocols. The genetic material was digested with the restriction enzyme SacI, and hybridizated with probes for bphC and bphD genes.

Similar results were observed using the two probes for bphC (a) and bphD (b). Only the size of the unique band in each case changes. The bph locus is located in the chromosome of strain JMS34, and not in the plasmid pJP4. This was determined by the absence of the bph locus in the plasmid pJP4. Therefore the plasmid pJP4 was transferred from the strains JMP134::X(pJP4-F3) and JMS34 to *E. coli* DH5α through biparental mating. The presence of bph locus in receptor strain was studied by kanamycin selection.

All analyzed *E. coli* transconjugants containing plasmid pJP4 were sensitive to kanamycin, indicating the absence of the bph locus in the plasmid. The bph locus is genetically stable in strain JMS34 during more than 100 generations in LB medium under non selective conditions.

The concentration ranges of biphenyl, 3-CBA, 4-CBA and 3,5-dCBA used as sole carbon and energy source for the growth of strain JMS34 were determined. Strain JMS34 were cultured in a K-salt minimal medium (Kröckel, L. and Focht D. D. 1987) supplemented with the corresponding carbon source at 30° C. during 72 hours. Cultures were incubated in test tubes in a volume of 2 ml.

FIG. 1 shows the growth observed. The axis of the abscissa indicates the concentration of biphenyl, 3-CBA, 4-CBA and 3,5-dCBA. The strain JMS34 was capable to grow using biphenyl in all the concentration range tested, i.e., at least until a biphenyl concentration of 18 mM. The growth using 3-CBA and 4-CBA as sole carbon and energy source is limited to a smaller concentration range, decreasing strongly at substrate concentrations above 10 mM. Strain JMS34 was unable to grow on 3,5-CBA as a sole carbon and energy source, at the tested concentrations.

In order to characterize the catabolic properties of the strain JMS34, degradation of CBAs and PCBs were analyzed.

Figure 2:
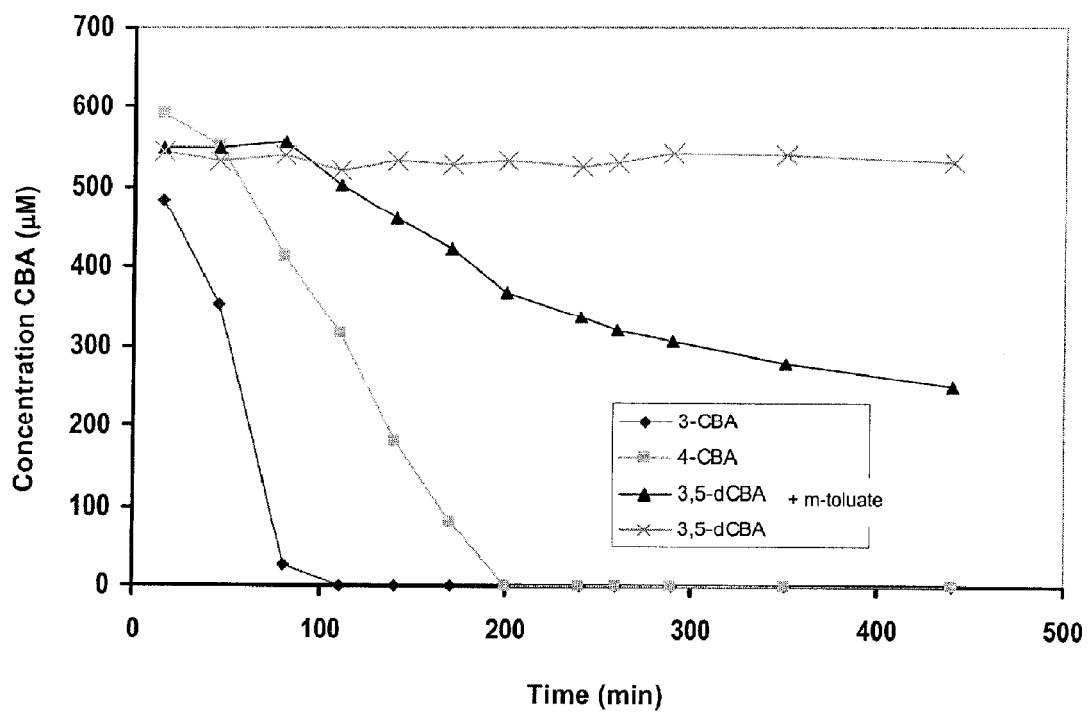
FIG. 2 shows the degradation kinetics of 3-CBA, 4-CBA, 3,5-dCBA and 3,5-dCBA in presence of m-toluate by the strain *Cupriavidus necator* JMS34.

FIG. 2 shows the degradation kinetics of 3-CBA, 4-CBA and 3,5-dCBA by the strain JMS34. Cultures of *Cupriavidus necator* JMS34 grown until exponential phase using fructose as single carbon and energy source, were incubated with CBAs. The concentration of the CBAs was determined by HPLC, using a wavelength of 230 nm and as mobile phase a mixture of methanol:acid orthophosphoric:water (80:0.5:19.5). Strain JMS34 efficiently degrades 3-CBA and 4-CBA. The degradation rate of 3-CBA was slightly higher. As described for growth, strain JMS34 was not capable to degrade 3,5-dCBA under these conditions. Nevertheless, strain JMS34 degrades 3,5-dCBA in presence of 3-methylbenzoate (m-toluate), which is a natural inducer of the xylX-YZL genes.

In an additional embodiment, the invention provides a treatment method for the bioremediation of an environment contaminated with PCBs. Environments such as soils, slurries, sediments and water contaminated by one or more PCB congeners are included in the invention.

In one embodiment of the invention, the bioremediation method includes the addition of a *Cupriavidus necator* strain JMS34 culture, to the PCB-polluted environment. The method of the invention include a certain period of time sufficient to permit the recombinant bacterium to completely degrade, i.e., to mineralize mono-, di- and trichlorinated PCBs.

For example, the recombinant bacterium can be added to an environment contaminated with PCBs, as an inoculum containing from about $10^4$ to about $10^9$ cells/ml in a saline medium. Then, for the degradation of the PCBs this bacterial strain is incubated in the PCB-contaminated environment during a period of time from about 1 week to 6 months, depending on the matrix properties.

The process of bioremediation described above can be periodically monitored by organic extractions of the contaminated matrix (with hexane, for example), and analyzing in the extract the presence of PCBs and/or degradation products. These extracts can be analysed, for example, by a chromatographic method. The degradation products can include $CO_2$, chlorobenzoic acids or their salts, chloride ion, as well as other metabolic products depending on the degradation of PCBs.

In an additional embodiment, the recombinant bacterium of the present invention can be added to a PCB-polluted environment, together with a compound that stimulate the degradation potential of this recombinant bacterium, e.g., a compound that induces the expression of xylXYZL genes, for a more efficient bioremediation of PCBs. For example, this compound can be m-toluate.

In a further embodiment, the above described contaminated environment corresponds to a matrix extracted from a contaminated environmental site, and relocated in a contained system. A contained system is a space, where the contaminated matrix does not have direct contact with the surrounding environment.

In the present invention the term "microcosms" refers to a certain volume of soil in a container (flask) whose important variables such as moisture and presence or absence of microorganisms and/or chlorinated organic pollutants are known and controlled.

Furthermore, the present invention relates to a product for the bioremediation of PCB-polluted environments, which includes a bacterial inoculum of strain *Cupriavidus necator* JMS34. This product for bioremediation contains an inoculum of the recombinant bacterium, at a concentration range from about $10^4$ to about $10^9$ cells/ml in a saline medium.

In an additional embodiment, the product for the bioremediation of PCB-polluted environments includes a bacterial inoculum of the strain *Cupriavidus necator* JMS34, where the bacterial cells are lyophilized, which facilitates its transport and commercialization.

In an additional embodiment, the product for the bioremediation of PCB-polluted environments includes a bacterial inoculum of *Cupriavidus necator* JMS34, where the bacterial cells are encapsulated in alginate. The encapsulation protects the bacterial cells and decreases its exposure to toxic compounds, increasing its stability and viability.

EXAMPLE 1

Degradation of PCBs by *Cupriavidus necator* JMS34

The capability of the strain JMS34 to completely degrade or mineralize four different congeners of PCBs: two monochlorinated biphenyls, 3-CB and 4-CB, and two dichlorinated biphenyls, 3,5-dCB and 2,4'-dCB (2,4'-dichlorobenzoate), which produce as metabolic intermediates 3-CBA, 4-CBA, 3,5-dCBA and 4-CBA, respectively, was evaluated. These CBAs can be degraded by strain JMS34. Resting cells of strain JMS34, previously grown in biphenyl or a mixture of biphenyl with m-toluate (3-methylbenzoate) and concentrated 10 times, were incubated during 72 h with PCB congeners. At the end of the incubation, the remaining PCB concentration in the medium, the type and the concentration of accumulated CBA, and the concentration of released chloride were determined. The chloride release is a consequence of the deshalogenation of the initial substrate, and therefore it represents a good parameter to evaluate the degradation of chlorinated compounds.

Figure 3:
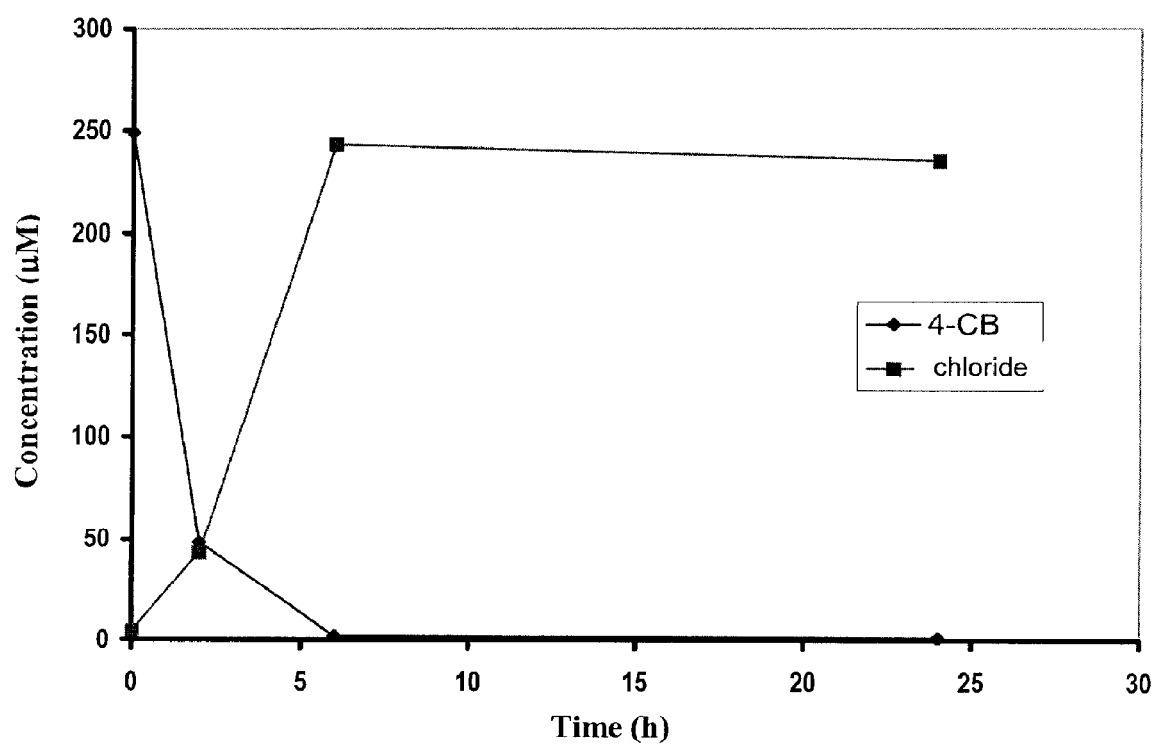
FIG. 3 shows the degradation of 4-CB by strain JMS34 and the chloride release during the degradation.

The degradation kinetics of 4-CB by strain JMS34 is shown in FIG. 3.

TABLE 1

| Substrate | Biphenyl | | | Biphenyl + m-toluate | | |
|---|---|---|---|---|---|---|
| | % CB | % CBA accumulated | % Chloride released | % CB | % CBA accumulated | % Chloride released |
| 3-CB | N.D. | 0 | 115 | N.D. | N.D. | 91 |
| 4-CB | N.D. | 0 | 123 | N.D. | N.D. | 125 |
| 3,5-dCB | N.D. | 52 | 76 | N.D. | 8.6 | 104 |
| 2,4'-CB | N.D. | 0 | 98 | N.D. | N.D. | 101 |

N.D.: not determined

Table 1. Degradation of diverse PCBs by *Cupriavidus necator* JMS34.

Cells grown in biphenyl were washed with K-salt medium, concentrated 10 times and incubated with chlorobiphenyl (0.5 mM) during 72 hours. The concentration of chlorobiphenyls, chlorobenzoates and chloride was determined.

K-salt medium is a free-chloride saline medium, which comprises salts of ammonium and phosphate minerals at very low concentrations (mineral traces) (Kröckel & Focht, 1987). This medium is used to carry out the subsequent chloride quantification.

Table 1 shows the results of the incubation of resting cells of strain JMS34 with the PCBs (0.5 mM). The incubations were carried out in a total volume of 1 mililiter in Schott test tubes. Strain JMS34 completly degrades 3-CB, 4-CB and 2,4'-dCB, without accumulating CBAs, and releasing stoichiometric amounts of chloride.

The complete degradation of 3,5-dCB was observed using resting cells previously grown in presence of m-toluate. Without the induction of the xyl genes by m-toluate, approximately 50% of 3,5-dCB is accumulated in the medium at the end of the incubation.

The strain *Cupriavidus necator* JMS34 is capable to degrade a wide range of PCBs not included in the above-described example, without accumulating CBA, such as 2,3'-dichlorobiphenyl (2,3'-dCB), 3,3'-dichlorobiphenyl (3,3'-dCB), 3,4'-dichlorobiphenyl (3,4'-dCB), 3,5,2'-trichlorobiphenyl (3,5,2'-tCB), 2,4,3'-trichlorobiphenyl (2,4,3'-tCB) and 2,4,4'-trichlorobiphenyl (2,4,4'-tCB).

In addition, due to the presence of locus bph of *Burkholderia xenovorans* LB400, the strain JMS34 is capable to degrade a wide range of PCBs with up to 6 chlorine substitutions.

EXAMPLE 2

Bioremediation of Soils Contaminated with PCBs

Diverse strategies for biorremediation of soils contaminated with PCBs have been described, from the induction of catabolic activities of the affected soil to addition of genetically modified microorganisms. In all cases relevant abiotic variable has to be controled such as amount and type of nutrients, inducing compounds, degradation promoting agents (for example, surfactants), aereation and temperature. The report by Gilbert and Crowley constitutes an example of bioremediation through the addition of a PCB-degrading bacterial strain to contaminated soils (Gilbert and Crowley 1998). A sandy soil of known physical and chemical properties was contaminated with of Aroclor 1242 (100 mg per gram of soil). Samples (20 grams) of contaminated soil were inoculated with the PCB-degrading strain *Arthrobacter* sp. B1B (3 ml) at a concentration of $10^8$ cells/ml. A saline solution without cells was added to control soils. The soil moisture was maintained at 12.5% throughout the period of incubation. Microcosms were kept under these conditions at an average temperature of 21° C. during 9 weeks. After the period of incubation the concentration of di-, tri-, tetra- and pentachlorinated PCBs decreased 88%, 40%, 11% and 3%, respectively. The control soils showed lower degradation for the di- and trichlorinated PCBs (34% and 13%, respectively). This study concludes that the addition of the aerobic bacterial strain *Arthrobacter* sp. B1B to a contaminated soil results in a significant decrease of the concentration of PCBs including trichlorinated biphenyls.

In order to obtain higher levels of PCB degradation it is useful to connect sequentially anaerobic processes of degradation (for dehalogenation of highly-chlorinated congeners) and aerobic processes.

EXAMPLE 3

Application Example

The capability of the strain JMS34 to degrade PCBs in contaminated soils was evaluated. For this purpose sterile and non-sterile microcosms were prepared and then contaminated with 3-CB, 4-CB, and 2,4'-dCB. These microcosms were inoculated with the strain JMS34 and strain LB400 to a final concentration of approximately $10^8$ colony forming units/g of soil. These systems were incubated at 30° C. with agitation during 63 days. In addition sterile and non-sterile control microcosms without inoculum were used. The sampling took place on days 0, 35 and 63 of the incubation period. Relevant variables such as moisture and bacterial concentration in the microcosms were evaluated every 15 days during the whole period of incubation.

The samples were extracted with hexane, concentrated and dried and then dissolved in a known final volume of the same solvent. Anthracene was used as internal standard. The concentration of PCBs in the samples was determined by gas chromatography and mass spectrometry (GC/MS).

The strains JMS34 and LB400 degrade efficiently more than 85% of the PCBs in less than 7 days of incubation. Strain JMS34 showed a higher yield, degrading at least 99% of the PCBs, i.e., showing higher PCB-degradation in a period of 7 days of incubation. Strain LB400 was able to degrade 85% in these conditions.

REFERENCES

Kröckel, L. and Focht D. D. 1987. Construction of chlorobenzene-utilizing recombinants by progenitive manifestation of a rare event. Appl. Environ. Microbiol. 53: 2470-2475.

Yao, Y., Takasuga, T., Masunaga, S, and Nakanishi J. 2002. Detailed study on the levels of polychlorinated dibenzo-p-dioxins, polychlorinated dibenzofurans and polychlorinated biphenyls in Yusho rice oil. Chemosphere. 46: 1461-1469.

Chen, Y. C., Guo, Y. L., Hsu, C. C. and Rogan W. J. 1992. Cognitive development of Yu-Cheng ("oil disease") children prenatally exposed to heat-degraded PCBs. J. Am. Med. Assoc. 268: 3213-3218.

Focardi, S., Fossi, C., Leoncio, C., Corsolini, S, and Parra O. 1996. Persistent organochlorine residues in fish and water birds from the Bio Bio river, Chile. Environ. Monitor. Assess. 43: 73-92.

Fuentealba, M. 1997. Pesticidas organochlorates y biphenyl policlorados en *Trachurus murphyi* en la zona centro stir de Chile. Bol. Soc. Biol. Concepción 68: 39-46

Ledger, Th., Pieper, D., Pérez-Pantoja, D. and González B. 2002. Novel insights into the interplay between peripheral reactions encoded by xyl genes and the chlorocatechol pathway encoded by tfd genes for the degradation of chlorobenzoates by *Ralstonia eutropha* JMP134. Microbiology 148:3431-3440.

Muñoz, J. and Becker, P. 1999. The Kelp Gull as bioindicator of environmental chemisclas in the Magellan region. A comparison with other coastal sites in Chile. Sci. Marina 63: 495-502.

Perez-Pantoja, D., Ledger, Th., Pieper, D. H. and Gonzalez, B. 2003. Efficient turnover of chlorocatechols is essential for growth of *Ralstonia eutropha* JMP134 (pJP4) in 3-chlorobenzoic acid. J. Bacteriol. 185: 1534-1542.

Barra R, Cisternas M, Suarez C, Araneda A, Pinones O, Popp P. 2004. PCBs and HCHs in a salt-marsh sediment record from South-Central Chile: use of tsunami signatures and 137Cs fallout as temporal markers. Chemosphere 55:965-72.

Diagnóstico nacional de contaminantes orgánicos persistentes: informe final. 2001. Centro Eula-Chile, Concepción.

Gilbert E. S, and Crowley D. E. 1998. Repeated application of carvone-induced bacteria to enhance biodegradation of polychlorinated biphenyls in soil. Appl. Microbiol. Biotechnol. 50: 489-494.

The invention claimed is:

1. A recombinant bacterium designated as *Cupriavidus necator* strain JMS34, deposited under the access number NRRL B-30817.

2. A product for the bioremediation of PCB-contaminated environments, including a bacterial inoculum of the strain according to claim 1 in an amount sufficient to degrade polychlorobiphenyls (PCB) contained in an environment into which the product is added.

3. The product for the bioremediation according to claim 2, wherein the inoculum contains from about $10^4$ to about $10^9$ cells/ml of *Cupriavidus necator* strain JMS34.

4. The product for the bioremediation according to claim 2, wherein the inoculum contains lyophilized cells of *Cupriavidus necator* strain JMS34.

5. The product for the bioremediation according to claim 2, wherein the inoculum contains cells of *Cupriavidus necator* strain JMS34 encapsulated in alginate.

6. The product for the bioremediation according to claim 2, wherein the bacterial inoculum has been cultivated in the presence of m-toluate as an inducer of the xylXYZL genes.

7. A method for the bioremediation of a PCB-contaminated environment containing polychlorobiphenyls (PCBs), comprising the steps of:
   a) adding recombinant bacterium designated as *Cupriavidus necator* strain JMS34, deposited under NRRL B-30817, as an inoculum to the PCB-contaminated environment, and
   b) incubating the recombinant bacterium in the environment for a period of time sufficient to degrade the PCBs in the environment.

8. A method according to claim 7, wherein the period of time ranges from 1 week to 6 months.

9. The method according to claim 8, wherein the PCB contain from 1 to 3 chlorine atoms.

10. The method according to claim 7, wherein the PCB is 3,5-dichlorobiphenyl, and wherein the recombinant bacterium has been cultivated in the presence of m-toluate as an inducer of the xylXYZL genes.

11. The method according to claim 10, wherein the inducer is 3-methylbenzoate (m-toluate).

12. The method according to claim 7 wherein the inoculum contains from about $10^4$ to about $10^9$ cells/ml of *Cupriavidus necator* strain JMS34.

13. The method according to claim 7 wherein the inoculum contains lyophilized cells of *Cupriavidus necator* strain JMS34.

14. The method according to claim 7 wherein the inoculum contains cells of *Cupriavidus necator* strain JMS34 encapsulated in alginate.

15. The method according to claim 7 wherein the recombinant bacterium has been cultivated in the presence of m-toluate as an inducer of the xylXYZL genes.

16. The method of claim 7, wherein the PCB is a molecule that contains from 1 to 3 chlorine atoms.

17. The method according to claim 7, wherein the PCB is selected from the group consisting of 3-chlorobiphenyl (3-CB), 4-chlorobiphenyl (4-CB), 2,4'-dichlorobiphenyl (2,4'-dCB), 2,3'-dichlorobiphenyl (2,3'-dCB), 3,3'-dichlorobiphenyl (3,3'-dCB), 3,4'-dichlorobiphenyl (3,4'-dCB), 3,5-dichlorobiphenyl (3,5-dCB), 3,5,2'-trichlorobiphenyl (3,5,2'-tCB), 2,4,3'-trichlorobiphenyl (2,4,3'-tCB) and 2,4,4'-trichlorobiphenyl (2,4,4'-tCB), and mixtures thereof.

18. The method according to claim 7, wherein the step of incubating completely degrades or demineralizes the compound 3-CB, 4-CB and 2,4'-dCB, without accumulating CBA compounds.

19. The method according to claim 7, wherein the step of incubating completely degrades or mineralizes the compound 3,5-dichlorobenzoate (3,5-dCBA).

* * * * *